United States Patent [19]

Borggrefe

[11] 4,002,676

[45] Jan. 11, 1977

[54] HYDROXYETHERCARBOXYLIC ACIDS

[75] Inventor: Gerhard Borggrefe, Dusseldorf, Germany

[73] Assignee: Henkel & Cie GmbH, Dusseldorf-Holthausen, Germany

[22] Filed: Jan. 28, 1972

[21] Appl. No.: 221,816

[30] Foreign Application Priority Data

Aug. 23, 1971 Germany ............................ 2142207

[52] U.S. Cl. ............................ 260/535 P; 252/110; 260/340.2; 260/501.18
[51] Int. Cl.² .................. C07C 59/14; C07C 59/12
[58] Field of Search ................................ 260/535 P

[56] References Cited

UNITED STATES PATENTS

| | | | |
|---|---|---|---|
| 2,311,008 | 2/1943 | Tucker | 260/535 P |
| 3,293,176 | 12/1966 | White | 260/519 X |
| 3,725,290 | 4/1973 | Nelson | 260/535 P |

Primary Examiner—Paul J. Killos
Attorney, Agent, or Firm—Hammond & Littell

[57] ABSTRACT

The present invention relates to a process for producing novel hydroxyether carboxylic acids and their salts containing at least one glycolic acid ether and at least two carboxylic acids as well as to these compounds per se.

8 Claims, No Drawings

HYDROXYETHERCARBOXYLIC ACIDS

THE PRIOR ART

Organic polycarboxylic acids having nitrogen or phosphorus atoms are known as sequestering agents for metal ions. Inorganic acids such as the polyphosphates are also known as sequestering agents for metal ions. These conventional sequestering agents, however, have become suspect as increasing the nitrogen and phosphorus content of waste waters leading to an imbalance in the ecology.

OBJECTS OF THE INVENTION

An object of the present invention is the development of compounds capable of sequestering metal ions, particularly alkaline earth metal ions, which compounds on degradation in waste waters do not give rise to nitrogen or phosphorus containing compounds.

A further object of the present invention is the development of hydroxyethercarboxylic acid compounds selected from the group consisting of (1) compounds having the formula

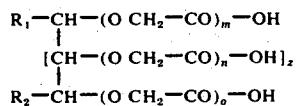

wherein $R_1$ and $R_2$ are members selected from the group consisting of hydrogen and —COOH, $z$ is an integer from 0 to 1 and $m$, $n$ and $o$ are integers from 0 to 1, with the provisos that said compound contains at least two carboxyl groups and at least one hydroxyl group in the molecule, at least one of $m$, $n$ and $o$ is 1, and when $R_1 = R_2$, $m$ and $o$ are not the same, and (2) their alkali metal, ammonium, lower alkylamine and lower alkylolamine salts.

A yet further object of the present invention is the development of a process for the production of said hydroxyethercarboxylic acids by reacting a corresponding hydroxy compound with an ester of a diazoacid in the presence of a Lewis acid catalyst and saponifying the resulting ester of an ethercarboxylic acid.

These and other objects of the present invention will become more apparent as the description thereof proceeds.

DESCRIPTION OF THE INVENTION

The above objects have been achieved by the development of a hydroxyethercarboxylic acid compound having the formula

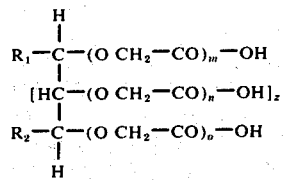

wherein $R_1$ is a member selected from the group consisting of hydrogen and carboxyl; wherein $R_2$ is a member selected from the group consisting of hydrogen and carboxyl, $R_1$ and $R_2$ being independent of each other; and wherein $z$ is 0 or 1; $m$ is 0 or 1; $n$ is 0 or 1; $o$ is 0 or 1; with the restrictions that at least one of $m$, $n$ or $o$ is 1, that at least two carboxyl groups and one hydroxyl group are present in the said compound, and that when $R_1 = R_2$, $m$ and $o$ are not the same. These acid compounds may be utilized per se or in the form of their salts capable of sequestering alkaline earth metal ions. More particularly, the invention relates to hydroxyethercarboxylic acid compounds selected from the group consisting of (1) compounds having the formula

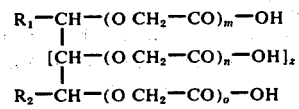

wherein $R_1$ and $R_2$ are members selected from the group consisting of hydrogen and —COOH, $z$ is an integer from 0 to 1 and $m$, $n$ and $o$ are integers from 0 to 1, with the provisos that said compound contains at least two carboxyl groups and at least one hydroxyl group in the molecule, at least one of $m$, $n$ and $o$ is 1, and when $R_1 = R_2$, $m$ and $o$ are not the same, and (2) their alkali metal, ammonium, lower alkylamine and lower alkylolamine salts.

The following are nonlimitive examples representative of the hydroxyethercarboxylic acid compounds, according to the invention:
- 1,2-bis-O-carboxymethyl glycerine
- mono-O-carboxymethyl glyceric acid
- mono-O-carboxymethyl tartaric acid
- mono-O-carboxymethyl erythric acid
- mono-O-carboxymethyl-1,2,3-trihydroxyglutaric acid
- 1,2-bis-O-carboxymethyl-1,2,3-trihydroxyglutaric acid The present invention also provides a process for the preparation of the hydroxyethercarboxylic acid compounds consisting essentially of the steps reacting (a) compounds of the formula

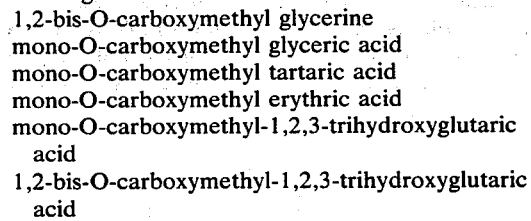

wherein $R_3$ is a member selected from the group consisting of hydrogen and carb-lower-alkoxy; wherein $R_4$ is a member selected from the group consisting of hydrogen and carb-lower-alkoxy, $R_3$ and $R_4$ being independent of each other; wherein X is a member selected from the group consisting of hydroxyl and halide; wherein $q$ is 0 or 1; with the restriction that at least 2 hydroxyl groups are present in the compound, (b) in the presence of a Lewis acid, with (c) diazoacetic acid esters of lower alkanols, in the molar ratio of (a) : (c) equaling 1 : 1 to 1 : (n—1) wherein $n$ equal the number of hydroxyl groups, to produce reaction products; saponifying the reaction products; and recovering the hydroxyether alkanedioic acids.

Among the starting compounds of the above formula are glycerine, glycerine-α-monochlorohydrin, lower alkyl esters of glyceric acid, tartaric acid, trihydroxyglutaric acid, and erythric acid, particularly the methyl and ethyl esters.

Among the diazoacetic acid esters, particularly the lower alkyl esters and primarily the ethyl ester, is utilized in the synthesis.

The O-alkylation of the above named starting substances with the calculated amount of diazoacetic acid ester is generally carried out at temperatures from −20° C to 30° C in the presence of Lewis acids, particularly of boric acid esters or boron trifluoride in the form of an ether adduct. From 0.5% to 10% of the catalyst, based on the hydroxyl group containing compound are usually employed.

If the starting materials at the reaction temperature are present as liquids, then the reaction may be carried out without solvents. If they are solids at reaction temperature, then solvents can be used which are inert under the reaction conditions, particularly the lower chlorinated hydrocarbons such as chloroform.

To work up the reaction mixture, water is first added, and the reaction products are then extracted with a water-insoluble solvent. The reaction product is isolated from the separated organic phase by distillation.

If the O-alkylation is carried out in the above described manner, the reaction products are mixtures of esters and lactones. The esters are comprised by esters of hydroxyethercarboxylic acids with lower alkanols. The lactones are comprised by dicarbalkoxy-dioxanones.

For example, in the reaction of diazoacetic acid ethyl ester with diethyl tartrate, the ester formed is mono-O-carboxymethyl diethyl tartrate with the following lactone also being formed: 5,6-dicarbethoxy-1,4-dioxanone-2 having the formula

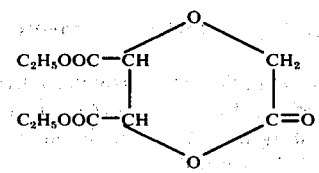

This lactone ring may be opened under the catalytic influence of sodium ethylate to give the named ester; or it may be opened under saponification conditions. In both cases the hydroxy tricarboxylic acid is formed.

Another embodiment for the preparation of compounds of the invention comprises reacting glycolic acid esters with epoxy compounds of an appropriate structure, such as epoxy-succinic acid esters, in the presence of known, particularly acidic alkoxylation catalysts, in a conventional way and saponifying the reaction products.

The saponification of the reaction products may be done in a conventional way, for instance with a 10% to 20% aqueous NaOH solution, whose amount is to be calculated so, that a 10% to 20% excess above the stoichiometrically required amount is present. The free ethercarboxylic acids are advantageously obtained from the resulting saponification solutions by passing the same through a strongly acidic cation exchanger, such as Lewatit S 100, and the eluate is concentrated under reduced pressure.

The substances, according to the invention, are usable per se or in the form of their salts as sequestering agents, particularly for calcium ions. The salts are preferably the alkali metal salts, such as the sodium or potassium salts, the ammonium salts, or the amine salts with lower alkylamines such as mono-, di-, or tri-methyl- or ethyl-amine, or with lower alkylolamines such as mono- or di- ethanol- or propanol- amine. Partial salts of alkaline earth metals which still retain sufficient carboxyl groups to sequester further alkaline earth metal ions may also be employed.

The corresponding complexes are stable over a wide pH-range. Such sequestering agents, free of N and P have the advantage in not having any nourishing effect on the flora of natural waters.

The following specific examples are illustrative of the invention without being deemed limitative in any respect.

EXAMPLE 1

(A) 114.1 gm (1 mol) of ethyl diazoacetate were added dropwise at a temperature range of 0° to 10° C with agitation to a mixture of 206.2 gm (1 mol) of diethyl tartrate and 14.6 gm (0.1 mol) of triethyl borate within 1 hour. The reaction mixture was further agitated and was maintained at room temperature for 12 hours and then subsequently distilled in vacuo. The fractions distilling over between 150° to 180° C. at 0.4 − 0.8 mm Hg pressure were redistilled at the same temperature and reduced pressure to produce 122.6 gm of a colorless oil that consisted of 2 components according to gas chromatography. By comparing the gas chromatogram with those of the test reference substance it could be ascertained that the reaction product consisted of mono-O-carbethoxymethyl diethyl tartrate (I) as the major component and of 5,6-dicarbethoxy-1,4-dioxanone-2(II) as the minor component. The percentage composition of the fractions, obtained by distillative working up, was, as follows:

| Boiling point in ° C and at 0.05 mm Hg | Refractive Index $n_D^{20}$ | Yield | | |
|---|---|---|---|---|
| | | gm. | % I | % II |
| 134 − 136 | 1.4470 | 24.1 | 75 | 23 |
| 136 − 133 | 1.4461 | 63.1 | 85.2 | 13.8 |
| 133 − 135 | 1.4461 | 24.6 | 86.6 | 12 |
| 135 − 145 | 1.4462 | 10.8 | 86.8 | 11.4 |

TEST SUBSTANCES a. 5,6-dicarbethoxy-1,4-dioxanone-2(II)

228.2 gm (2 mols) of ethyl diazoacetate were added in portions at room temperature to a mixture of 412.4 gm (2 mols) of diethyl tartrate and 29.2 gm (0.2 mols) of triethyl borate. Sufficient portions of the diazoacetate were added such that after each addition the solution became decolorized. After the reaction mixture had been left standing for 10 days at room temperature, a high-vacuum distillation was carried out. 373 gm of a colorless distillate were obtained from which 82.8 gm of a colorless product gradually crystallized out. The remaining liquid product was distilled off, and the remaining oil was redistilled. From the fractions, distilling over between 130°–180° C at 0.05 mm Hg pressure, another 37.2 gm of colorless product crystallized out. The combined crystallizates were recrystallized from ethanol. Colorless crystals having a melting point of 79° to 80° C resulted. The recrystallized product was found to be pure by gas chromatography.

Molecular-weight determination (by osmometry)

Calculated: 246.2. Found: 252 (in benzene). $C_{10}H_{14}O_7(246.2)$

Calculated: C, 48.78%; H, 5.73%; O, 45.49%; Sap. No. 682. Found: C, 48.98%; H, 5.56%; O, 45.77%; Sap. No. 695.

The oil remaining after separation of the lactone(II) consisted substantially of 23% of lactone(II), according to the gas chromatographical analysis, and of 66% of the diester(I) according to (b) (1) infra.

b. (1) Mono-O-carbethoxymethyl diethyl tartrate(I)

20 gm (0.08 mol) of the lactone(II) were added to a dilute solution of sodium ethylate in 200 ml of ethanol. After standing for several hours at room temperature the mixture had become concentrated; and the residue was dissolved in ether. The ether solution was washed with water, then dried and concentrated. The residual oil was distilled in vacuo 15.4 gm (65% of the theory) of a colorless oil of a b.p. between 147° to 150° C at 0.4 mm Hg pressure and of the refractive index $n_D^{20} = 1.4460$ were obtained.

$C_{12}H_{20}O_8$ (292.29)

Calculated: C, 48.98%; H, 7.11%; O, 43.73%. Found: C, 49.00%; H, 6.91%; O, 43.98%.

Mass spectrum: m/e 294 (molecular mass + 1 proton) IR(film) OH = 3497 cm$^{-1}$ (2.86 μ)

(B) (1) 40 gm (0.16 mol) of the lactone(II) were added to a solution of 23.2 gm(0.58 mol) of NaOH in water. Homogenization immediately occurred. After standing for 1 hour at room temperature the solution was run through a cation-exchanger (Lewatit S 100). From the concentrated eluate, after drying over $P_2O_5$, 31 gm (92% of theory) of colorless crystalline mono-O-carboxymethyl-tartaric acid could be isolated.

Water, according to Karl Fischer: 2.5% $H_2O$ Mass spectrum: m/e 208 (molecular mass) $C_6H_8O_8$ (208.13)

Calculated: C, 34.63%; H, 3.87%; O, 61.50%; Acid No. 808. Found: C, 34.07%; H, 4.01%; O, 61.11%; Acid No. 780.

(B) (2) 54.5 gm of the mixture, obtained according to Example 1(A) of the compounds (I) and (II) were added to a solution of 24.7 gm (0.62 mol) NaOH in 150 ml of water. The solution was heated for 1 hour at 50° C; and after cooling the solution was subsequently lead through a ion exchanger (Lewatit S 100). From the concentrated eluate, 37.5 gm of a colorless viscous residue of mono-O-carboxymethyl tartaric acid were isolated, that crystallized gradually after drying over $P_2O_5$ at room temperature.

Water according to Karl Fischer: 5.9%. Acid No.: Calc.: 808 Found: 752.

EXAMPLE 2

(A) 2 ml of a $BF_3$-ether complex were added to a solution of 110 gm (1 mol) of glycerin-α-monochlorohydrin in 150 ml of chloroform. Subsequently 250 gm (2.2 mol) of ethyl diazoacetate were added dropwise thereto at −20° C. After the $N_2$ evolution had terminated the mixture was washed with water until a neutral pH was achieved. The mixture was concentrated by distillation in vacuo. 156.2 gm (55% of theory) of a colorless oil of bis-(O-carbethoxymethyl-glycerine-α-monochlorohydrin were obtained having a b.p. between 127° to 133° C at 0.15 − 0.2 mm Hg pressure. The index of refraction $n_D^{20}$ was between 1.4509 and 1.4510. A sample was redistilled for the analysis and had a b.p. of 131° C at 0.1 mm Hg and the $n_D^{20}$ was 1.4509.

$C_{11}H_{19}O_6Cl$ (282.7)

Calculated: C, 46.73%; H, 6.77%; O, 33.95%; Cl, 12.54%. Found: C, 46.70%; H, 6.84%; O, 34.22%; Cl, 12.40%.

(B) 56.4 gm (0.2 mol) of bis-O-carbethoxymethyl-glycerin-α-monochlorohydrin were added to a solution of 68 gm of KOH in 400 ml of water. The solution was heated at 80° C until homogenized. The solution was then acidified; the aqueous phase was concentrated; and the remaining residue was extracted with acetone. After concentrating the acetone phase, a colorless oil was isolated therefrom which was found to be free of halogen. The 1,2-bis-O-carboxymethyl-glycerine was found to have an acid number of 561, while the calculated acid number was 538. The higher acid number results from a partial lactonizing in acidic solution. The calculated acid number for the lactone was 590.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

I claim:

1. A hydroxyethercarboxylic acid compound selected from the group consisting of (1) a compound selected from the group consisting of 1,2-bis-O-carboxymethyl glycerine, mono-O-carboxymethyl glyceric acid, mono-O-carboxymethyl tartaric acid, mono-O-carboxymethyl erythric acid, mono-O-carboxymethyl-1,2,3-trihydroxyglutaric acid, and 1,2-bis-O-carboxymethyl-1,2,3-trihydroxyglutaric acid; and (2) a salt of said compound selected from the group consisting of alkali metal salts, ammonium salts, lower alkylamine salts, and lower akylolamine salts.

2. A hydroxyethercarboxylic acid compound selected from the group consisting of (1) a compound selected from the group consisting of mono-O-carboxymethyl-tartaric acid, mono-O-carboxymethyl-1,2,3-trihydroxyglutaric acid, and 1,2-bis-O-carboxymethyl-1,2,3-trihydroxyglutaric acid; and (2) a salt of said compound selected from the group consisting of alkali metal salts, ammonium salts, lower alkylamine salts, and lower alkylolamine salts.

3. Mono-O-carboxymethyl-tartaric acid.

4. 1,2-bis-O-carboxymethyl-glycerine.

5. Mono-O-carboxymethyl glyceric acid.

6. Mono-O-carboxymethyl erythric acid.

7. Mono-O-carboxymethyl-1,2,3-trihydroxyglutaric acid.

8. 1,2-bis-O-carboxymethyl-1,2,3-trihydroxyglutaric acid.

* * * * *